(12) United States Patent
Denholm et al.

(10) Patent No.: US 7,273,875 B2
(45) Date of Patent: Sep. 25, 2007

(54) NAPHTHYRIDINE DERIVATIVES, THEIR PREPARATION AND THEIR USE AS PHOSPHODIESTERASE ISOENZYME 4 (PDE4) INHIBITORS

(75) Inventors: Alastair Denholm, Rochestown (IE); Thomas H Keller, Singapore (SG); Clive McCarthy, Basel (CH); Neil J Press, West Sussex (GB); Roger J Taylor, West Sussex (GB)

(73) Assignee: Novartis AG, Basel (CH)

( * ) Notice: Subject to any disclaimer, the term of this patent is extended or adjusted under 35 U.S.C. 154(b) by 72 days.

(21) Appl. No.: 10/494,223

(22) PCT Filed: Nov. 4, 2002

(86) PCT No.: PCT/EP02/12300

§ 371 (c)(1),
(2), (4) Date: May 3, 2004

(87) PCT Pub. No.: WO03/039544

PCT Pub. Date: May 15, 2003

(65) Prior Publication Data

US 2004/0254212 A1    Dec. 16, 2004

(30) Foreign Application Priority Data

Nov. 5, 2001  (GB)  ................................ 0126511.5
Apr. 30, 2002 (GB)  ................................ 0209882.0

(51) Int. Cl.
*A61K 31/4375* (2006.01)
*C07D 471/04* (2006.01)

(52) U.S. Cl. ...................... 514/300; 546/122
(58) Field of Classification Search ............... 546/122; 514/300
See application file for complete search history.

(56) References Cited

U.S. PATENT DOCUMENTS 5,126,344 A * 6/1992 Roberts et al. ............. 514/248
6,136,821 A * 10/2000 Hersperger ................ 514/300

FOREIGN PATENT DOCUMENTS

| JP | 2002-114684 | 4/2002 |
|---|---|---|
| WO | 98/18796 | 5/1998 |
| WO | 99/18077 | 4/1999 |

OTHER PUBLICATIONS

Lehner et al., Principle of Biochemistry, 204 (Worth Publishers, 2nd Edition 1993) (1982).*
Pascal et al., Synthesis and Structure-Activity Relationships of 4-Oxo-1-phenyl-3,4,6,7-tetrahydro-[1,4]diazepino[6,7,1-hi]indoles: Novel PDE4 Inhibitors, Bioorg. Med. Chem. Lett., 10:35-38 (2000).*
Iwasaki et al., Novel Selective PDE IV Inhibitors as Antiasthmatic Agents. Synthesis and Biologicval Activities of a Series of 1-Aryl-2,3-bis(hydroxymethyl)naphthalene Lignans, J. Med. Chem., 39: 2696-2704 (1996).*
Norman P. "PDE4 inhibitors 1999" Exp. Opin. ther. patents 9(8)1101-1118 (1999).*
Hersperger et al. "Palladium catalyzed cross coupling . . . " J. Med. Chem. 43 p. 675-682 (2000).*
Hersperger et al., "Pd-Catalysed Cross-Coupling Reactions for the Synthesis of 6,8-Disubstituted 1,7-Naphtyridines: A Novel Class of Potent and Selective Phosphodiesterase Type 4D Inhibitors", Journal of Medicinal Chemistry, vol. 43, pp. 675-682 (2000).
Souness et al., "Proposal for Pharmacologically Distinct Conformers of PDE4 Cyclic AMP Phosphodiesterases", Cell. Signal., vol. 9, No. 3/4, pp. 227-236 (1997).

* cited by examiner

*Primary Examiner*—Celia Chang
(74) *Attorney, Agent, or Firm*—Gregory C. Houghton

(57) ABSTRACT

The invention relates to compounds of formula I

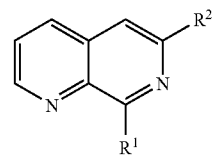

in free or salt form, where $R^1$ is a monovalent aromatic group having up to 10 carbon atoms, and $R^2$ is a cycloaliphatic group having up to 8 ring carbon atoms. Compositions containing them, methods for their preparation and their use as pharmaceuticals are also described.

14 Claims, No Drawings

NAPHTHYRIDINE DERIVATIVES, THEIR PREPARATION AND THEIR USE AS PHOSPHODIESTERASE ISOENZYME 4 (PDE4) INHIBITORS

This invention relates to organic compounds, their preparation and their use as pharmaceuticals.

In one aspect, the present invention provides compounds of formula I

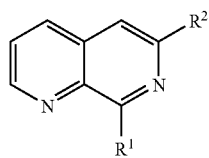

in free or salt form, where
$R^1$ is a monovalent aromatic group having up to 10 carbon atoms, and
$R^2$ is a cycloaliphatic group having up to 8 ring carbon atoms.

"$C_1$-$C_8$-alkyl" as used herein denotes straight chain or branched $C_1$-$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$-$C_8$-alkyl is $C_1$-$C_4$-alkyl.

"$C_1$-$C_8$-alkoxy" as used herein denotes straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$-alkoxy.

"$C_1$-$C_8$-alkylthio" as used herein denotes straight chain or branched $C_1$-$C_8$-alkylthio, which may be, for example, methylthio, ethylthio, n-propylthio, isopropylthio, n-butylthio, isobutylthio, sec-butylthio, tert-butylthio, straight or branched pentylthio, straight or branched hexylthio, straight or branched heptylthio, or straight or branched octylthio. Preferably, $C_1$-$C_8$-alkylthio is $C_1$-$C_4$-alkylthio.

"$C_1$-$C_8$-haloalkyl" as used herein denotes $C_1$-$C_8$-alkyl as hereinbefore defined substituted by one or more halogen atoms, preferably one, two or three halogen atoms.

"$C_1$-$C_8$-haloalkoxy" as used herein denotes $C_1$-$C_8$-alkoxy as hereinbefore defined substituted by one or more halogen atoms, preferably one, two or three halogen atoms.

"$C_3$-$C_8$-cycloalkyl" as used herein denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably "$C_3$-$C_8$-cycloalkyl" is cyclopropyl, cyclobutyl, cyclopentyl, cyclohexyl, cycloheptyl or cyclooctyl.

"Acyl" as used herein denotes alkylcarbonyl, for example $C_1$-$C_8$-alkylcarbonyl where $C_1$-$C_8$-alkyl may be one of the $C_1$-$C_8$-alkyl groups hereinbefore mentioned, optionally substituted by one or more halogen atoms; cycloalkylcarbonyl, for example $C_3$-$C_8$-cycloalkylcarbonyl where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl, tetrahydrofurylcarbonyl, pyrrolidinylcarbonyl, piperidinylcarbonyl or pyridylcarbonyl; arylcarbonyl, for example $C_6$-$C_{10}$-arylcarbonyl such as benzoyl; or aralkylcarbonyl, for example $C_6$ to $C_{10}$-aryl-$C_1$-$C_4$-alkylcarbonyl such as benzylcarbonyl or phenylethylcarbonyl.

"$C_1$-$C_8$-alkoxycarbonyl" as used herein denotes $C_1$-$C_8$-alkoxy as hereinbefore defined linked through an oxygen atom thereof to a carbonyl group.

"$C_1$-$C_8$-haloalkoxycarbonyl" as used herein denotes $C_1$-$C_8$-haloalkoxy as hereinbefore defined linked through an oxygen atom thereof to a carbonyl group.

"$C_1$-$C_8$-hydroxyalkoxycarbonyl" and "$C_1$-$C_8$-alkoxy-$C_1$-$C_8$-alkoxycarbonyl" as used here denote $C_1$-$C_8$-alkoxycarbonyl as hereinbefore defined in which the $C_1$-$C_8$-alkoxy group is substituted by hydroxy or a further $C_1$-$C_8$-alkoxy group respectively.

"Carboxy-$C_1$-$C_8$-alkoxy" as used herein denotes $C_1$-$C_8$-alkoxy as hereinbefore defined substituted by carboxy.

"Halogen" or "halo" as used herein may be fluorine, chlorine, bromine or iodine; preferably it is fluorine, chlorine or bromine.

$R^1$ may be, for example, phenyl optionally substituted by one or more electron-withdrawing substituents, preferably selected from cyano, halogen, carboxy, aminocarbonyl, $C_1$-$C_8$-haloalkyl or $C_1$-$C_8$-haloalkoxy, preferably one or two such substituents, and/or optionally substituted by $C_1$-$C_8$-alkyl, hydroxy, $C_1$-$C_8$-alkoxy or $C_1$-$C_8$-alkylthio, or $R^1$ may be a heterocyclic aromatic group having up to 10 ring atoms and 1 to 4 ring hetero atoms, preferably selected from nitrogen, oxygen and sulfur, for example a heterocyclyl group such as furyl, thienyl, pyrrolyl, imidazolyl, pyrazolyl, furazanyl, triazolyl, tetrazolyl, oxazolyl, isoxazolyl, thiazolyl, pyridyl, pyrimidyl, pyridazinyl, triazinyl, indolyl, isoindolyl or benzimidazolyl, which heterocyclyl group may be unsubstituted or substituted e.g. by at least one $C_1$-$C_8$-alkyl, halogen or $C_1$-$C_8$-alkoxy. Preferred groups $R^1$ include (a) phenyl substituted by cyano, halogen (particularly fluorine or chlorine), carboxy or $C_1$-$C_4$-haloalkoxy, and optionally by $C_1$-$C_4$-alkyl or $C_1$-$C_4$-alkoxy, (b) phenyl substituted by $C_1$-$C_4$-alkoxy and (c) an aromatic heterocyclic group having 5 or 6 ring atoms and one or two ring hetero atoms.

$R^2$ may be, for example, a $C_3$-$C_8$-cycloalkyl group such as cyclopropyl, methylcyclopropyl, cyclobutyl, cyclopentyl, methylcyclopentyl, cyclohexyl, methylcyclohexyl, dimethylcyclohexyl, cycloheptyl, bicycloheptyl or cyclooctyl, optionally substituted by at least one substituent selected from $C_1$-$C_8$-alkyl, $C_1$-$C_8$-alkoxy, carboxy, $C_1$-$C_8$-alkoxycarbonyl, $C_1$-$C_8$-haloalkoxycarbonyl, $C_1$-$C_8$-hydroxyalkoxycarbonyl, $C_1$-$C_8$-alkoxy-$C_1$-$C_8$-alkoxycarbonyl, aminocarbonyl, $C_1$-$C_8$-alkylarminocarbonyl, di($C_1$-$C_8$-alkyl)aminocarbonyl, hydroxy, acyl or $C_1$-$C_8$-alkyl optionally substituted by hydroxy, cyano, carboxy or $C_1$-$C_8$-alkoxycarbonyl. Preferably, $R^2$ is $C_5$-$C_7$-cycloalkyl substituted by $C_1$-$C_4$-alkyl, carboxy, $C_1$-$C_8$-alkoxy-carbonyl or aminocarbonyl.

Preferred compounds of formula I in free or salt form include those where
$R^1$ is phenyl substituted by one or two substituents selected from cyano, halogen, carboxy or aminocarbonyl, and optionally by $C_1$-$C_8$-alkoxy, or $R^1$ is phenyl substituted by $C_1$-$C_4$-alkoxy, hydroxy or $C_1$-$C_4$-alkylthio, and
$R^2$ is $C_3$-$C_8$-cycloalkyl optionally substituted by at least one substituent selected from $C_1$-$C_4$-alkyl, carboxy, $C_1$-$C_8$-alkoxycarbonyl or aminocarbonyl.

Further preferred compounds of formula I in free or salt form include those where R$^1$ is phenyl substituted by one of two substituents selected from cyano, halogen, carboxy or aminocarbonyl meta to the indicated naphthyridine ring and optionally by C$_1$-C$_4$-alkoxy ortho to the indicated naphthyridine ring, or R$^1$ is phenyl substituted by C$_1$-C$_4$-alkoxy meta to the indicated naphthyridine ring, and R$^2$ is C$_5$-C$_7$-cycloalkyl optionally substituted by at least one substituent selected from carboxy and C$_1$-C$_4$-alkoxycarbonyl.

Other preferred compounds of formula I in free or salt form include those where

R$^1$ is phenyl optionally substituted by one, two or three substituents selected from the group consisting of halo, cyano, C$_1$-C$_8$-alkyl, C$_1$-C$_8$-alkylthio, —SO—C$_1$-C$_8$-alkyl, C$_1$-C$_8$-alkoxy and C$_1$-C$_8$-haloalkoxy, or phenyl fused with a heterocyclic ring having 3 to 8 ring atoms of which up to 4 can be carbon atoms and up to 4 can be hetero atoms; and R$^2$ is C$_5$-C$_8$-cycloalkyl optionally substituted by at least one substituent selected from the group consisting of carboxy and carboxy-C$_1$-C$_8$-alkoxy, Further preferred compounds of formula I in free or salt form include those where R$^1$ is phenyl optionally substituted by one, two or three substituents selected from the group consisting of halo, cyano, C$_1$-C$_4$-alkyl, C$_1$-C$_4$-alkylthio, —SO—C$_1$-C$_4$-alkyl, C$_1$-C$_4$-alkoxy and C$_1$-C$_4$-haloalkoxy, or phenyl fused with a heterocyclic ring having 5 or 6 ring atoms of which up to 4 can be carbon atoms and up to 2 can be hetero atoms; and R$^2$ is C$_5$-C$_7$ cycloalkyl optionally substituted by at least one substituent selected from the group consisting of carboxy and carboxy-C$_1$-C$_4$-alkoxy.

The compounds represented by formula I are capable of forming acid addition salts, particularly pharmaceutically acceptable acid addition salts. Pharmaceutically acceptable acid addition salts of the compounds of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid.

These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

The compounds of formula I in free or salt form may exist in stereoisomeric forms according to the orientation of moieties attached to the cycloaliphatic ring. The invention embraces both individual such stereoisomers, i.e. cis and trans isomers, as well as mixtures thereof. Where R$^1$ or R$^2$ contain an asymmetric carbon atom, the compounds of formula I in free or salt form exist in individual optically active isomeric forms or as mixtures thereof, e.g. as racemic or diastereomeric mixtures. The invention embraces both individual optically active R and S isomers as well as mixtures, e.g. racemic or diastereomeric mixtures, thereof.

Specific especially preferred compounds of formula I are those described hereinafter in the Examples.

The present invention also provides a process for the preparation of compounds of formula I in free or salt form which comprises (i) (A) reacting a compound of formula II

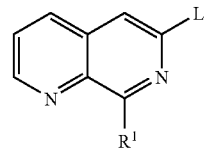

II optionally in protected form, where R$^1$ is as hereinbefore defined and L is a leaving atom or group, for example halogen or an aliphatic or aromatic sulfonyloxy group such as trifluoromethylsulfonyloxy, with a compound of formula III

 III optionally in protected form, where R$^2$ is as hereinbefore defined and X is a leaving atom or group which is reactive with L in formula II to form a direct bond between R$^2$ and the indicated naphthyridine ring, followed by deprotection if required;

(B) reacting a compound of formula I, where R$^2$ is cycloalkyl substituted by a C$_1$-C$_8$-alkoxycarbonyl group, to convert the alkoxycarbonyl group into a carboxy group;

(C) for the preparation of compounds of formula I where R$^2$ is a cycloaliphatic group substituted by carboxy-C$_1$-C$_8$-alkoxy, hydrolysing a compound of formula I where R$^2$ is a cycloaliphatic group substituted by C$_1$-C$_8$-alkoxycarbonyl-C$_1$-C$_8$-alkoxy; or (D) for the preparation of compounds of formula I when R$^1$ is phenyl substituted by —SO—C$_1$-C$_8$-alkyl, oxidising a compound of formula I where R$^1$ is phenyl substituted by C$_1$-C$_8$-alkylthio; and (ii) recovering the product in free or salt form.

Where L in formula II is an aromatic sulfonyloxy group, X may be, for example, a group YM- where Y is halogen such as iodine and M is a metal such as zinc or magnesium.

Process variant (A) may be effected using known procedures for reaction of leaving atoms or groups or analogously, for example as hereinafter described in the Examples. Where X in formula III is YM-, the compound YMR$^2$ may be formed in situ by reaction of the metal M and the halide YR$^2$; where M is zinc, this in situ reaction is conveniently effected in the presence of dibromoethane and a trialkylsilyl halide, preferably in a solvent, e.g. an ether such as tetrahydrofuran (THF), convenient reaction temperatures being from 25 to 50° C. Reaction of the compound of formula II with YMR$^2$ may be effected in the presence of a transition metal catalyst, particularly a palladium-ketone complex catalyst, 1,1'-bis(diphenyl-phosphino)ferrocene and a quaternary ammonium halide such as tetrabutylammonium iodide, conveniently in a solvent, e.g. a mixture of an ether such as THF and N-methyl-pyrrolidone(NMP), convenient reaction temperatures being from 25 to 50° C. Where it is desired to minimise the possibility of reaction of functional groups other than those participating in the desired reaction, such functional groups may be protected by conventional protecting groups.

Process variant (B) may be effected using known procedures for conversion of alkoxycarbonyl groups to carboxy groups, e.g. hydrolysis with an aqueous alkali metal hydroxide, or analogously such as hereinafter described in the Examples.

Process variant (C) may be effected using art known procedures for the hydrolysis of esters to carboxylic acids, e.g. using trifluoroacetic acid, or analogously such as hereinafter described in the Examples.

Process variant (D) may be effected using art known procedures for the oxidation of sulfanyl groups to sulfinyl groups, e.g. using ozone or hydrogen peroxide, or analogously such as hereinafter described in the Examples.

Compounds of formula II may be prepared as described in WO98/18796 or analogously, for example as hereinafter described in the Examples. Compounds of formula III may be prepared by known procedures, for example in situ as described hereinbefore and (in the Examples) hereinafter.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley &c Sons Inc, Second Edition, 1991, which reference also describes procedures suitable for replacement of the protecting groups by hydrogen.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I in free or salt form are useful as pharmaceuticals. Accordingly the invention also provides a compound of formula I in free or salt form for use as a pharmaceutical. The compounds of formula I in free or salt form, hereinafter referred to alternatively as "AGENTS OF THE INVENTION", exhibit cyclic nucleotide phosphodiesterase (PDE) isoenzyme inhibiting activity, selective for type 4 isoenzyme. AGENTS OF THE INVENTION possess anti-inflammatory, anti-airways hyperreactivity and bronchodilator properties. They further possess immunosuppressive and TNFα secretion inhibitory activities. The pharmacological activities may be demonstrated in test methods, for example as follows:

PDE4 Isoenzyme Inhibition Assay

Cloning: GATEWAY flanked PDE4 cDNA constructs containing the coding regions of the three isoenzymes, human PDE4A, human PDE4B, and human PDE4D are generated by PCR and transposed into the GATEWAY shuttle vector pDONOR-201. In addition a 6-histidine tag is introduced by PCR onto the carboxyl terminal end of each of the constructs to facilitate protein purification. Following sequence verification, the PDE4 constructs are transposed into the GATEWAY expression vector pDEST-8, Positive recombinants are selected and transposed into *E. coli* strain DH10Bac and bacmid produced transfected into SF21 cells using Bac-To-Bac (Invitrogen Life Technologies). Positive transfections are selected and used to generate high titer viral stocks for use in protein expression.

PDE4 Expression: Sf21 cells are grown to a density of $2\times10^6$ cells/ml and infected with human PDE4A, PDE4B or PDE4D3 containing baculovirus to a multiplicity of infection (m.o.i.) of 1 for 72 hours. The infected cells are harvested by centrifugation at 1,400 g for 4 minutes at 4° C. and the cell pellets are frozen at −80° C. Sf21 (*Spodoptera frugiperda* 21) insect cells are routinely maintained at densities between $3\times10^5$ and $3\times10^6$ cells/ml in SF00 Serum Free Medium (Invitorgen Life Technologies). Sf21 cells ($1\times10^9$) are resuspended in 100 ml cold (4° C.) Lysis Buffer (50 mM $Na_2HPO_4$, 200 mM NaCl, 10 mM Imidazole). Cells are incubated on ice for 30 minutes then centrifuged at 15,000 g for 20 minutes at 4° C.

PDE4 Purification: The 6 Histidine-tagged PDE4 proteins are isolated from crude cell lysates by a batch-wise Ni-NTA purification strategy (QIAGEN). N-NTA resin is first pre-rinsed to remove ethanol preservative and equilibrated with Lysis Buffer. Cell lysate is added, (10 ml 50% Ni-NTA slurry resin per 50 ml lysate), and gently rotated on a mixer at 4° C. for 1-2 hours. The sample is then centrifuged at 1,000 g for 5 minutes at 4° C. using Denley benchtop centrifuge. The supernatant is removed and the resin is washed 3 times with 50 ml ice cold Wash Buffer (50 mM $Na_2HPO_4$, 300 mM NaCl and 20 mM imidazole) followed by centrifugation at 1,000 g for 5 min at 4° C. The 6His-tagged protein is eluted from the resin with 3×5 ml ice cold Elution Buffer (50 mM $NaH_2PO_4$, 300 mM NaCl, 250 mM imidazole) and collected by centrifugation at 1,000 g for 5 minutes at 4° C. The supernatants are then pooled before buffer exchange and concentration using a VivaScience 20 ml SK 0.2 µM Concentrator. Samples are aliquoted and stored at −20° C.

SDS-PAGE Electrophoresis: Purified PDE4 samples are analysed by SDS-PAGE using 8-16% gradient mini-gels (Novex) and samples are denatured at 100° C. in reducing sample buffer (62 mM Tris-HCl pH 6.8, 10% glycerol, 3% SDS, 5% β-mercaptoethanol, 0.02% bromophenol blue) for 3 min prior to loading. Novex SeeBlue pre-stained MW standards are also loaded. Gels are run at a constant 25 mA. Gels are stained with GelCode Colloidal Coomassie G-250 Blue Stain Reagent (Pierce) according to the manufacturer's procedure.

Western Blot Analysis: Samples are analysed on Novex 8-16% gradient gels as described above. The gel is then wet blotted onto Millipore Immobilon-P PVDF membrane using the tank transfer method with 25 mM Tris-HCl pH 8.8, 192 mM Glycine, 15% methanol transfer buffer at 80 mA for 16 h. Immunoprobing is carried out in TTBS buffer (20 mM Tris-HCl pH 7.6, 0.9% (w/v) NaCl, 0.05% (v/v) Triton X-100, 0.5% (w/v) casein) with an anti-6his monoclonal antibody (QIAGEN) at 1:1000 dilution, An anti-mouse IgG alkaline phosphatase conjugate is used as the secondary antibody (Sigma A9919) at 1:10000 dilution and proteins visualised with BCIP/NBT substrate prepared from tablets (Sigma) according to the manufacturers procedure, PDE4 Assay: The assay is based on Amersham Pharmacia Biotech Scintillation Proximity Assay (SPA) technology. Enzyme is diluted with enzyme dilution buffer (10 mM Tris-HCl, pH7.5 containing 1 mM EDTA) in order to obtain between 10-30% total substrate hydrolysis during the assay.

The enzymatic reaction is started by adding 10 μl diluted enzyme to 80 μl substrate (0.1 μCi [3H]-cAMP, 1 μM cAMP) and 10 μl inhibitor solution in a 96-well microtiter plate. After 30-60 minutes incubation at room temperature the reaction is stopped by adding 50 μl PDE SPA beads (20 mg/ml). After 30 minutes the plate is centrifuged (3000 g, 10 minutes) and counted (Packard TopCount).

Inhibitor stock solutions are prepared in 100% dimethylsulphoxide (DMSO) and diluted with DMSO/water to achieve 10 concentrations to cover the range of 0-100% inhibition. The concentration of DMSO is kept constant at 1% (v/v) throughout the assay.

The concentration at which 50% inhibition occurs ($IC_{50}$) is determined from inhibition—concentration curves in a conventional manner. Within the PDE4 isoenzyme group, AGENTS OF THE INVENTION generally exhibit selectivity for inhibition of PDE4D isoenzyme relative to PDE4A, PDE4B and PDE4C. The compounds of Examples 1, 3, 10, 12, 14 and 15 have $IC_{50}$ values of 38, 9, 25, 21, 57 and 9 nM respectively for inhibition of PDE4D in the above assay.

Having regard to their inhibition of binding of PDE4, AGENTS OF THE INVENTION are useful in the treatment of conditions mediated by PDE4, particularly inflammatory conditions. Treatment in accordance with the invention may be symptomatic or prophylactic.

Accordingly, AGENTS OF THE INVENTION are useful in the treatment of inflammatory or obstructive airways diseases, resulting, for example, in reduction of tissue damage, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial or viral infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Having regard to their anti-inflammatory activity, their influence on airways hyperreactivity and their profile in relation to PDE isoenzyme inhibition, in particular as selective type 4 inhibitors, AGENTS OF THE INVENTION are useful for the treatment, in particular prophylactic treatment, of obstructive or inflammatory airways disease. Thus by continued and regular administration over prolonged periods of time AGENTS OF THE INVENTION are useful in providing advance protection against recurrence of bronchoconstrictor or other symptomatic attack consequential to obstructive or inflammatory airways disease or for the control, amelioration or reversal of basal status of such disease.

Having regard to their bronchodilator activity AGENTS OF THE INVENTION are useful as bronchodilators, e.g. for the treatment of chronic or acute broncho-constriction, e.g. for the symptomatic treatment of obstructive or inflammatory airways disease.

Having regard to their activity as selective inhibitors of TNF-α release, AGENTS OF THE INVENTION are also useful for the down-regulation or inhibition of TNF-α release, e.g. for the treatment of diseases or conditions in which TNF-α release is implicated or plays a mediating role, e.g. diseases or conditions having an aetiology involving or comprising morbid, for example undesirable, excessive or unregulated TNF-α release, in particular for the treatment of cachexia or endotoxin shock and in treatment of AIDS [cf. Sharief et al, Mediators of Inflammation, 1 323-338 (1992)], the treatment of cachexia associated with morbid TNF-α release or TNF-α blood-serum levels of whatever origin, including cachexia consequential to, e.g. bacterial, viral or parasitic, infection or to deprivation or deterioration of humoral or other organic, e.g. renal function, the treatment of cancerous, malarial and vermal cachexia, cachexia resulting from dysfunction of the pituitary, thyroid or thymus glands as well as uremic cachexia and, in particular, the treatment of AIDS-related cachexia, i.e. cachexia consequential to or associated with to HIV infection.

The method of the invention is also applicable to the treatment of septic shock, e.g., shock conditions resulting from bacterial infection. In this regard it is to be noted that the present invention provides a method for the treatment of septic shock as such as well as of conditions consequential to or symptomatic of septic or shock, for example ARDS.

The AGENTS OF THE INVENTION are further applicable to the treatment of disease consequential to HIV infection, e.g. AIDS, e.g. to the amelioration or control of the advance of such disease.

Having regard to their profile in relation to inhibition of PDE isoenzymes and/or TNF-α release inhibition, as well as their immunosuppressive activity, AGENTS OF THE INVENTION are also useful as immunosuppressive agents, e.g. for the treatment of autoimmune diseases, in particular for the treatment of autoimmune diseases in which inflammatory processes are implicated or which have an inflammatory component or aetiology, or as anti-inflammatory agents for the treatment of inflammatory disease in particular for the treatment of inflammatory disease in which autoimmune reactions are implicated or which have an autoimmune component or aetiology. Examples of such disease to which the present invention is applicable include autoimmune hematological disorders (e.g. hemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine ophthalmopathy, Grave's disease, sarcoidosis, alveolitis, chronic hypersensitivity pneumonitis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), as well as inflammatory and/or hyperproliferative skin diseases such as psoriasis, atopic dermatitis, pemphigus and, in particular, contact dermatitis, e.g. allergic contact dermatitis.

AGENTS OF THE INVENTION are in particular useful for the treatment of arthritis, and other rheumatic or inflammatory disease, especially for the treatment of rheumatoid arthritis.

As immunosuppressants AGENTS OF THE INVENTION are further useful in the prevention of graft rejection, e.g. for the maintenance of allogenic organ transplants or the like, e.g. in relation to kidney, liver, lung, heart, heart-lung, bowel, bone-marrow, skin, or corneal transplant.

Having regard to their profile in relation to inhibition of PDE isoenzymes, in particular their profile as selective type 4 inhibitors, AGENTS OF THE INVENTION are further useful for the treatment of disease involving tissue calcium depletion, in particular degenerative diseases of the bone and joint involving calcium depletion, especially osteoporosis. In this regard they are further useful for the treatment of allergic inflammatory diseases such as rhinitis, conjunctivitis, atopic dermatitis, urticaria and gastrointestinal allergies; as vasodilators, e.g. for the treatment of angina, hypertension, ischaemia/reperfusion injury, congestive heart failure and multi-infarct dementia; and for the treatment of other conditions where inhibition of PDE 4 is indicated, for example, depression, conditions and diseases characterised by impaired cognitive function including Alzheimer's disease, Parkinson's disease and stroke.

The AGENTS OF THE INVENTION are also useful as co-therapeutic agents in combination with other drug substances such as anti-inflammatory, bronchodilatory, antihistamine or immunosuppressive drug substances, particularly in the treatment of inflammatory diseases e.g. obstructive or inflammatory airways diseases, autoimmune diseases or graft rejection such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700 and LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®-AstraZeneca). Such bronchodilatory drugs include anticholinergic or antimuscarinic agents, in particular ipratropium bromide, oxitropium bromide and tiotropiurm bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO 00/175114, which document is incorporated herein by reference, preferably compounds of the Examples thereof, especially a compound of formula

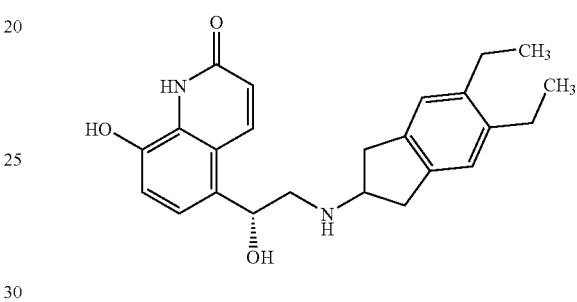

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Co-therapeutic immunosuppressive drug substances include, e.g. cyclopeptide, cyclopeptolide or macrolide drug substances, for examples drugs belonging to the cyclosporin class, e.g. cyclosporins A or G, the drug substances tacrolimus (also known as FK 506), ascomycin and rapamycin and their various known congeners and derivatives.

Combinations of AGENTS OF THE INVENTION and steroids, beta-2 agonists, or LTD4 antagonists may be used, for example, in the treatment of COPD or, particularly, asthma. Combinations of AGENTS OF THE INVENTION and anticholinergic or antimuscarinic agents, PDE4 inhibitors, dopamine receptor agonists or LTB4 antagonists may be used, for example, in the treatment of asthma or, particularly, COPD. Combinations of AGENTS OF THE INVENTION and immunosuppressive drug substances may be used in the treatment of any disease or condition requiring immunosuppressive treatment as hereinbefore described.

Other useful co-therapeutic combinations of AGENTS OF THE INVENTION include combinations with PDE3 inhibitors such as those disclosed in WO 00/166123, e.g. revizinone, ci-lostamide, amipizone, siguazodan, carbazeran, bemoradan, motapizone and, particularly, milrinone, enoximone and pimopendan, especially for treatment of conditions characterised by acute or chronic obstruction of vessels and/or bronchi and/or acute or chronic inflammation, e.g. acute obstructive bronchitis, bronchial asthma or COPD.

In accordance with the foregoing, the present invention also provides a method for the treatment of a disease mediated by PDE4 which comprises administering to a subject, particularly a human subject, in need thereof an effective amount a compound of formula I, or a pharmaceutically acceptable salt thereof, as hereinbefore described. In another aspect, the invention provides a compound of formula I, or a pharmaceutically acceptable salt thereof, as hereinbefore described for use in the preparation of a medicament for the treatment of a disease mediated by PDE4.

In accordance with the foregoing, the present invention also provides a method for the treatment of an inflammatory disease, particularly an obstructive or inflammatory airways disease, which comprises administering to a subject, particularly a human subject, in need thereof an effective amount a compound of formula I, or a pharmaceutically acceptable salt thereof, as hereinbefore described. In another aspect, the invention provides a compound of formula I, or a pharmaceutically acceptable salt thereof, as hereinbefore described for use in the preparation of a medicament for the treatment of an inflammatory disease, particularly an obstructive or inflammatory airways disease.

The AGENTS OF THE INVENTION may be administered by any appropriate route, e.g. orally, for example in the form of a tablet or capsule; parenterally, for example intravenously; topically to the skin, for example in the treatment of psoriasis; intranasally, for example in the treatment of rhinitis; or by inhalation, particularly in the treatment of obstructive or inflammatory airways diseases.

In a further aspect, the invention also provides a pharmaceutical composition comprising as active ingredient a compound of formula I in free form or in the form of a pharmaceutically acceptable salt thereof, optionally together with a pharmaceutically acceptable diluent or carrier therefor. Such compositions may be prepared using conventional diluents or excipients and techniques known in the galenic art. Thus oral dosage forms may include tablets, capsules and controlled release formulations such as encapsulated or matrix dissolution formulations, osmotic system formulations or ion exchange resin formulations. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose.

When the composition comprises a dry powder formulation, it preferably contains, for example, a compound of formula I having a particle diameter up to 10 microns, optionally together with a diluent or carrier, such as lactose, of the desired particle size distribution and a compound that helps to protect against product performance deterioration due to moisture.

When the composition comprises a nebulised formulation, it preferably contains, for example, a compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages employed in practising the invention will of course vary depending, for example, on the particular condition to be treated, the effect desired and the mode of administration. In general, suitable daily dosages for oral administration are of the order of 0.5 to 200 mg, while suitable daily dosages for administration by inhalation are of the order of from 0.1 to 10 mg.

The invention is illustrated by the following Examples. 6-Amino-8-bromo-1,7-naphthyridine used in the Examples is prepared as described in WO98/18796.

EXAMPLE 1

4[8-(3-Cyano-phenyl)-[1,7]naphthyridin-6-yl]-cyclohexanecarboxylic acid ethyl ester 6-amino-8-(3-cyanophenyl)-1,7-naphthyridine To a mixture of tetrahydrofuran (THF) (80 ml) and 2 N sodium carbonate (34 ml, aqueous) is added 6-amino-8-bromo-1,7-naphthyridine (4.007 g), triphenylphosphine (0.37 g) and 3-cyanophenylboronic acid (323 g). The mixture is degassed under argon three times and then bis (dibenzylideneacetone)palladium (0) (0.4 g) is added and the mixture is degassed under argon three more times. The mixture is heated at 80° C. under argon for 16 hours then cooled and filtered. The mixture is diluted with ethyl acetate and washed with 2 N sodium hydroxide then brine. After drying over sodium sulfate the organic layer is evaporated and suspended in ether. The solid precipitate thus obtained is the title compound, which is filtered off. M.p. 182-184° C. HRMS $[M+H]^+$ found=247.1.

6-Trifluromethanesulfonyl-8-(3 cyanophenyl)-1,7-naphthyridine—Compound A

To a solution of 6-amino-8-(3-cyanophenyl)-1,7-naphthyridine (4.058 g) in dimethylform-amide (DMF) (22 ml) under argon at 0° C. is added trifluoromethanesulfonic acid (11 ml). The mixture is stirred at 0° C. for 10 minutes and then sodium nitrite (2.26 g) is added slowly. The cooling bath is then removed and the mixture stirred at room temperature for 3 hours. The resulting mixture is diluted with ethyl acetate and washed with water, 2 M NaOH and water again. The organic layer is dried over sodium sulfate, then concentrated in vacuo and purified by column chromatography, eluting with 10:0.5 toluene:acetone to yield the title compound. M.p. 102-104° C. MS (m/e)=380.1

4-Iodo-cyclohexanecarboxylic acid ethyl ester—Compound B

To a cold (0° C.) stirred solution of 4-hydroxy-cyclohexanecarboxylic acid ethyl ester (1.0 g, 5.80 mmol) in 1:2 $CH_2Cl_2/CCl_4$ (52 ml) is added triphenylphosphine (1.82 g, 6.96 mmol), imidazole (473 mg, 6.96 mmol), and iodine (1.79 g, 7.08 mmol). The reaction is allowed to warm to room temperature and stirred overnight. The reaction is quenched by the addition of saturated sodium thiosulphate (c.a. 50 ml) and stirred until the solution becomes clear. The layers are separated and the aqueous layer is extracted with $CH_2Cl_2$ (3×30 ml). The combined organic phases are washed with sodium thiosulphate (30 ml), brine (30 ml), dried with anhydrous $MgSO_4$, filtered and evaporated at reduced pressure to an oily solid. Purification by dry flash chromatography, Keiselgel 15-40 grade silica, eluting with 3% ethyl acetate/iso hexane yields the title compound as a clear colourless oil.

4-[8-(3-Cyano-phenyl)-[1,7]naphthyridin-6-yl]-cyclohexanecarboxylic acid ethyl ester A flask is charged with activated zinc dust (742 mg, 11.13 mmol), THF (1.80 ml) and 1,2-dibromoethane (25 µl 0.284 mmol). The suspension is heated to reflux for 3 minutes and then allowed to cool before trimethylsilyl chloride (29 µl, 0.227 mmol) is added. The mixture is stirred for 15 minutes, then Compound B (1.60 g, 5.67 mmol) is added and the mixture stirred at 35° C. for 1.5 hours. A second flask is charged with Pd (dibenzylideneacetone)$_2$ (101 mg, 0.176 mmol), 1,1'-bis(diphenyl-phosphino)ferrocene (98 mg, 0.176 mmol), N-methylpyrrolidinone (NMP) (3 ml):THF (1 ml), tetrabutylammonium iodide (2.79 g, 7.56 mmol) and Compound A (956 mg, 2.52 mmol and the contents are added to the first flask at 35° C. The reaction is stirred for 2 hours, then quenched by the addition of water (15 ml) and stirred for ten minutes. Ethyl acetate (40 ml) is then added and stirred for 5 minutes. The layers are separated and the organic layer is washed with 5% citric acid (25 ml), water (2×25 ml), and brine (40 ml), dried with anhydrous MgSO$_4$, filtered and evaporated to brown viscous oil. Purification is by dry flash chromatography using 15-40 grade Keiselgel silica, eluting with 30% ethyl acetate/iso-hexane to yield the title compound as an orange gum. MH$^+$ 386.0.

EXAMPLE 2

4-[8-(3-Cyano-phenyl)-[1,7]naphthyridin-6-yl]-cyclohexanecarboxylic acid

A solution of lithium hydroxide (6.5 mg, 0.155 mmol) in water (160 µl) is added to a solution of 4-[8-(3-cyano-phenyl)-[1,7]naphthyridin-6-yl]-cyclohexane carboxylic acid ethyl ester (60 mg, 0.155 mmol) in NMP(0.16 ml). Upon completion, the reaction is diluted with water and washed with ethyl acetate (5 ml). The aqueous layer is acidified with 5% citric acid and the product is extracted into ethyl acetate. The organic layer is dried over brine (10 ml) and anhydrous MgSO$_4$, filtered and evaporated. Purification by flash chromatography using Keiselgel 40-63 grade silica and eluting with 1.5% CH$_3$OH:0.5% CH$_3$COOH: dichloromethane affords the title compound. MH$^+$ 357.0. mp 179.8-180.3° C.

EXAMPLE 3

4-[8-(3-Cyano-phenyl)-[1,7]naphthyridin-6-yl]-cyclohexanecarboxylic acid

Potassium Salt

4-[8-(3-Cyano-phenyl)-[1,7]naphthyridin-6-yl]-cyclohexanecarboxylic acid (24 mg, 0.067 m mol)) is dissolved in methanol (c.a. 2 ml) and anhydrous K$_2$CO$_3$ (4.6 mg, 0.035 mmol) is added. The suspension is ultra-sonicated for 15 minutes or until the K$_2$CO$_3$ is dissolved. Evaporation of the methanol and subsequent trituration of the resulting salt with both ethyl acetate and diethyl ether followed by drying gives the title compound. MH$^+$ 357.0 (parent acid). Mp>250° C.

EXAMPLE 4

4-[8-(3-Carbamoyl-pheny4)-[1,7]naphthyridin-6-yl]-cyclohexanecarboxylic acid Sodium hydroxide (4 M, 0.5 ml) is added to a solution of 4-[8-(3-cyano-phenyl)-[1,7]naphthyridin 6-yl]-cyclohexanecarboxylic acid ethyl ester (65 mg, 0.168 mmol) in NMP/CH$_3$OH/H$_2$O (0.50 ml, 8:1:1) and the solution is left stirring overnight. The solution is acidified with aqueous 5% citric acid and extracted into ethyl acetate (3×10 ml). The organic layer is dried over brine, anhydrous MgSO$_4$, filtered and evaporated at reduced pressure to a yellow gum. Purification is by mass spectrometry guided preparative HPLC (column: Xterra ms c8 5 µm 19×50 mm) to give the title compound. MH$^+$ APCI 376.0.

EXAMPLE 5

3-[6-(4-Carboxy-cyclohexyl)-[1,7]naphthyridin-8-yl]-benzoic acid

This is prepared analogously to Example 4, purification by mass spectrometry guided preparative HPLC (column: Xterra c8 5 µm 19×50 mm) affording the title compound. MH$^+$ APCI 377.1

EXAMPLE 6

4-[8-(5-Fluoro-2-methoxy-phenyl)-[1,7]naphthyridin-6-yl]-cyclohexanecarboxylic acid ethyl ester This is prepared analogously to Example 1, from trifluoromethanesulfonic acid 8-(5-fluoro-2-methoxy-phenyl)-[1,7]-naphthyridin-6-yl ester as the starting material. MH+ APCI 409.0.

EXAMPLE 7

4-[8-(5-Fluoro-2-methoxy-phenyl)-[1,7]naphthyridin-6-yl]-cyclohexanecarboxylic acid This is prepared, analogously to Example 2, from the product of Example 6, the product being purified by mass spectrometry guided HPLC (column: Xterra ms c8 5 µm 19×50 mm) to give the title compound as a yellow gum. MH$^+$ 381.1.

EXAMPLE 8

4-[8-(5-Fluoro-2-methoxy-phenyl)-[1,7]naphthyridin-6-yl]-cyclohexanecarboxylic acid sodium salt This is prepared, analogously to Example 3, from the product of Example 7, using anhydrous Na$_2$CO$_3$. MH$^+$ 381.1 (parent acid seen).

EXAMPLES 9-19

By procedures analogous to the appropriate Examples above, and using appropriate starting materials, compounds of formula I are obtained as identified in Table I together with mass spectrometry characterising data (MS:APCI MH$^+$). The compounds are obtained in free form, except for Example 11 that is isolated as the potassium salt.

TABLE I
| Ex. No | R¹ | R² | MS |
|---|---|---|---|
| 9 | 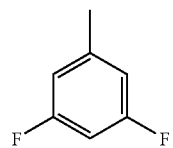 | 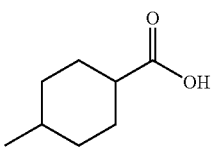 | 368.6 |
| 10 | 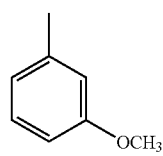 | 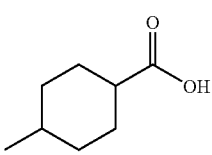 | 362.9 |
| 11 | 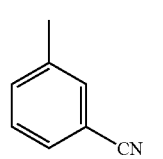 | 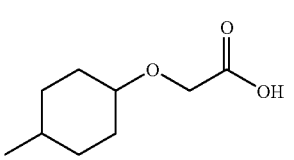 | 388.184 |
| 12 | 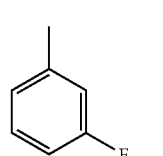 | 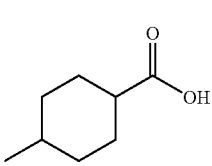 | 350.6 |
| 13 | 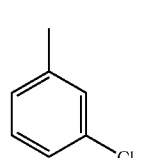 | 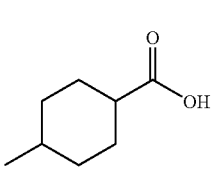 | 367.0 |
| 14 | 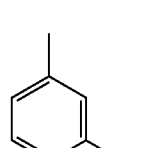 | 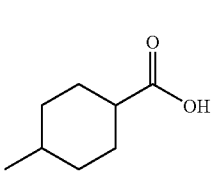 | 417.65 |
| 15 | 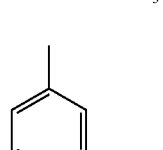 | 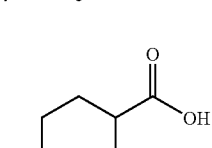 | 379.05 |
| 16 | 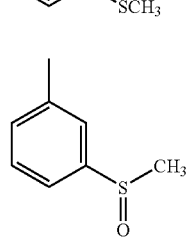 | 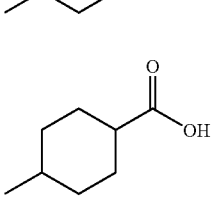 | 395.87 |
| 17 | 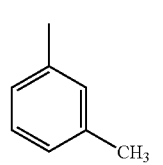 | 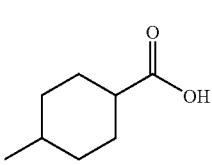 | 347.06 |

TABLE I-continued

| Ex. No | R¹ | R² | MS |
|---|---|---|---|
| 18 | 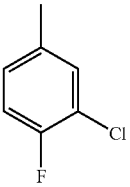 | 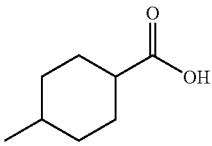 | 386.8 |
| 19 | 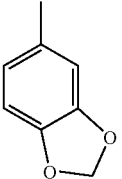 | 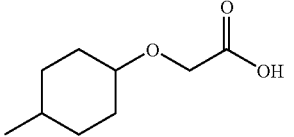 | 407.16 |
| 20 | 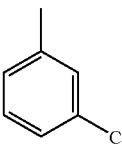 | 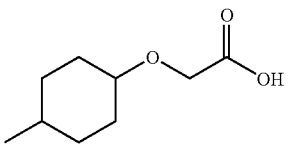 | 377.12 |
| 21 | 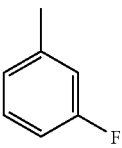 | 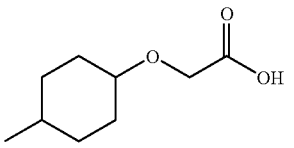 | 381.16 |
| 22 | 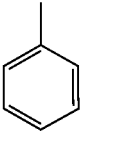 | 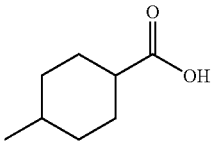 | 333.71 |

EXAMPLE 10

4-[8-(3-Methoxy-phenyl)-[1,7]naphthyridin-6-yl]-cyclohexanecarboxylic acid

Potassium hydroxide (2 M, 0.9 ml) is added to a solution of 4-[8-(3-Methoxy-phenyl)-[1,7]naphthyridin-6-yl]-cyclohexanecarboxylic acid ethyl ester (230 mg, 0.6 mmol) in THF/ethanol (6 ml:2 ml) and heated at 80° C. for 3 hours. The solution is then diluted with ethyl acetate (120 ml) and extracted with water. The aqueous layer is taken to pH 4 with 1M HCl to give a white precipitate, which is extracted into dichloromethane (DCM). The DCM layer is washed with water, then dried over magnesium sulfate, filtered and concentrated to yield the desired product. M.p 209-212° C. MS (AP$^+$) 362.9

4-[8-(3-Methoxy-phenyl)-[1,7]naphthyridin-6-yl]-cyclohexanecarboxylic acid ethyl ester This compound is prepared in an analogous way to compound 4-[8-(3-Cyano-phenyl)-[1,7]naphthyridin-6-yl]-cyclohexanecarboxylic acid ethyl ester from trifluoromethanesulfonic acid 8-(3-methoxy-phenyl)-[1,7]naphthyridin-6-yl ester. Purification is by chromatography followed by trituration with ether to yield a white solid. MS (AP$^+$) 391.0

Trifluoromethanesulfonic acid 8-(3-methoxy-phenyl)-[1.7]naphthyridin-6-yl ester

This compound is prepared in an analogous way to Compound A. MS (TOF ES+) 384.97

EXAMPLE 11

Potassium {4-[8-(3-cyano-phenyl)[1,7] naphthyridin-6-yl]-cyclohexyloxy}-acetate

Potassium carbonate (10.1 mg, 0.074 mmol) in water (1 ml) is added to a solution of {4-[8-(3-cyano-phenyl)-[1,7] naphthyridin-6-yl]cyclohexyloxy}-acetic acid (59 mg, 0.15 mmol) in methanol (6 ml). The reaction mixture is stirred at room temperature for 30 minutes, filtered and concentrated. The product is lyophilised from water (×3) then dried at 40° C. in vacuo for 18 hours. Recrystallisation from CH$_2$Cl$_2$/ether gives the product. m.p 148-150° C. (decomp.) MS (ES$^+$) [M+H]$^+$ 388.1635

{4-[8-(3-cyano-phenyl)-[1.7]naphthyridin-6-yl]-cyclohexyloxy}-acetic acid

Trifluoroacetic acid (TFA) (2 ml) is added to a solution of {4-[8-(3-cyano-phenyl)-[1,7]naphthyridin-6-yl]-cyclohexyloxy}-acetic acid tert-butyl ester (182 mg, 0.41 mmol) in CH$_2$Cl$_2$ (2 ml) at 0° C. The solution is stirred at room temperature for 1 hour, concentrated, and azeotroped with toluene (×3). Purification by chromatography on silica gel, eluting with 7% methanol in CH$_2$Cl$_2$ gives the product. MS (ES$^+$) [M+H]$^+$ 388.04

{4-[8-(3-cyano-phenyl)-[1,7]naphthyridin-6-yl]-cyclohexyloxy}-acetic acid tert-butyl ester 1,2-Dibromoethane (12 µl) is added to a slurry of zinc dust (589 mg, 9.0 mmol) in tetrahydrofuran (THF) (0.9 ml), The mixture is heated at reflux for 3 minutes then allowed to cool to room temperature. trimethylsilylchloride (TMSCl) (15 µl) is added and the mixture is stirred at room temperature for 30 minutes. (4-iodo-cyclohexyloxy)-acetic acid tert-butyl ester (cis:trans=ca. 1:1) (680 mg, 2.0 mmol) in THF (1 ml) is added via syringe and the mixture is heated at 40° C. for 2 hours. A solution of Bu$_4$NI i.e. tetrabutylammonium iodide (1.1 g, 3.0 mmol), Pd(dba)$_2$ i.e. palladium dibenzylideneacetone (40 mg, 0.07 mmol), dppf i.e. 1,1'-bis(diphenylphosphino)ferrocene (39 mg, 0.07 mmol) and Compound A (372 mg, 1.0 mmol) in THF (2 ml)/NMP(2 ml) is added and the mixture is heated at 40° C. for 18 hours then allowed to cool to room temperature. The reaction mixture is diluted with ethyl acetate and filtered over Celite. The filtrate is washed with sat. aq. NH$_4$Cl (×1), 10% aq. citric acid (×1), water (×1) and brine (×1), dried (MgSO$_4$), filtered and concentrated. Purification by chromatography on silica gel, eluting with 30% ethyl acetate in isohexane gives the trans product. MS (ES$^+$) [M+H]$^+$ 444.10

(4-iodo-cyclohexyloxy)-acetic acid tert-butyl ester

Triphenylphosphine (1.18 g, 4.49 mmol), imidazole (0.31 g, 4.49 mmol) and iodine (1.14 g, 4.49 mmol) are added to a solution of (4-hydroxy-cyclohexyloxy)-acetic acid tert-butyl ester (cis:trans=ca. 1:1) (0.86 g, 3.74 mmol) in a mixture of CH$_2$Cl$_2$ (10 ml)/CCl$_4$ (20 ml) at 0° C. The cooling bath is removed and the reaction mixture is stirred at room temperature for 18 hours. Saturated aq. Na$_2$S$_2$O$_3$ (10 ml) is added and the mixture is stirred for 15 minutes. The layers are separated and the aqueous layer is re-extracted with CH$_2$Cl$_2$ (×3). The combined organic extracts are washed with brine (×1), dried (Na$_2$SO$_4$), filtered and concentrated. Purification by chromatography on silica gel, eluting with 5% ethyl acetate in isohexane, gives the product.

EXAMPLE 12

4-[8-(3-Fluorophenyl)-[1,7]naphthyridin-6-yl]-cyclohexanecarboxylic acid

Lithium hydroxide (1M (aq), 24.3 ml, 24.3 mmol) is added to a solution of 4-[8-(3-fluorophenyl)-[1,7]naphthyridin-6-yl]-cyclohexanecarboxylic acid ethyl ester (4.60 g, 12.14 mmol) in THF/methanol (40 ml:20 ml) and stirred at room temperature overnight. The organic solvents are removed by evaporation, then the aqueous residue diluted with water and basified to pH9 with 1M KOH. The aqueous layer is then washed with ethyl acetate (3×). The aqueous layer is acidified to pH 4 with 1M HCl to give a white precipitate, which is extracted into ethyl acetate. The ethyl acetate layer is then dried over sodium sulfate, filtered and concentrated to yield the desired product as a yellow foam. Further trituration with 1M HCl yields the product as a pale yellow powder (2.153 g). MS (AP$^+$) 350.6

4-[8-(3-Fluorophenyl)-[1,7]naphthyridin-6-yl]-cyclohexanecarboxylic acid ethyl ester This compound is prepared in an analogous way to compound 4-[8-(3-cyano-phenyl)-[1,7]naphthyridin-6-yl]-cyclohexanecarboxylic acid ethyl ester from trifluoromethanesulfonic acid 8-(3-flurophenyl)-[1,7]naphthyridin-6-yl ester. Purification is by chromatography followed by trituration with ether to yield a white solid. MS (AP$^+$) 378.98

Trifluoromethanesulfonic acid 8-(3-fluorophenyl)-[1,7]naphthyridin-6-yl ester

This compound is prepared in an analogous way to Compound A. MS (TOF ES+) 372.87

EXAMPLE 14

4-[8-(3-Trifluoromethoxyphenyl)-[1,7]naphthyridin-6-yl]-cyclohexanecarboxylic acid Potassium hydroxide (2M (aq), 2.5 ml) is added to a solution of 4-[8-(3-trifluoromethoxyphenyl)-[1,7]naphthyridin-6-yl]-cyclohexanecarboxylic acid ethyl ester (250 mg, 0.56 mmol) in ethanol (10 ml) and stirred 45° C. for 1 h. The reaction mixture is diluted with water and acidified with c.HCl to pH3. The mixture is stirred for 2 h. then filtered, and the filter cake washed with water to yield the product as a white powder (218 mg). MS (AP$^+$) 417.65

4-[8-(3-Trifluoromethoxyphenyl)-[1,7]naphthyridin-6-yl]-cyclohexanecarboxylic acid ethyl ester This compound is prepared in an analogous way to compound 4-[8-(3-cyano-phenyl)-[1,7]naphthyridin-6-yl]-cyclohexanecarboxylic acid ethyl ester from trifluoromethanesulfonic acid 8-(3-trifluromethoxyphenyl)-[1,7]naphthyridin-6-yl ester. Purification is by chromatography followed by trituration with ether to yield a white solid. MS (AP$^+$) 445

Trifluoromethanesulfonic acid 8-(3-fluorophenyl)-[1,7]naphthyridin-6-yl ester

This compound is prepared in an analogous way to Compound A. MS (TOF ES+) 438.3

EXAMPLE 15

4-[8-(3-Methylsulfanyl-phenyl)-[1,7]naphthyridin-6-yl]-cyclohexanecarboxylic acid Lithium hydroxide (168 mg, 1.76 mmol) in water (1.7 ml) is added to a solution of 4-[8-(3-methylsulfanyl-phenyl)-[1,7]naphthyridin-6-yl]-cyclohexanecarboxylic acid ethyl ester (650 mg, 1.6 mmol) in THF (3.2 ml) under argon. Methanol is added to maintain solution (4 ml) and the mixture is stirred at room temperature for 5 hours. The mixture is evaporated to dryness then partitioned between ethyl acetate and water. The aqueous layer is acidified to pH 2 then extracted into ethylacetate and dried over magnesium sulfate, Evaporation gives a green gum which is reevaporated from methanol then DCM/diethylether to give a yellow/green foam. The foam is triturated with 3:1 hexane:diethyl ether, 2:1 hexane: diethylether, ethylacetate/hexane/ether mixtures and finally 5:1 diethylether:ethanol to yield an off-white solid. This is then recrystallised from ethanol to yield the title compound. M.p 177.6-178.2° C., MS (AP+) 379.05

4-[8-(3-Methylsulfanyl-phenyl)-[1,7]-naphthyridin-6-yl]-cyclohexanecarboxylic acid ethyl ester This compound is prepared in an analogous way to 4-[8-(3-cyano-phenyl)-[1,7]naphthyridin-6-yl]-cyclohexanecarboxylic acid ethyl ester from the analogous starting materials. MS (AP+) 407.2

EXAMPLE 16

4-[8-(3-Methanesulfinyl-phenyl)-[1,7]naphthyridin-6-yl]-cyclohexanecarboxylic acid A solution of 4-[8-(3-Methanesulfanyl-phenyl)-[1,7] naphthyridin-6-yl]-cyclohexanecarboxylic acid (30 mg, 0.079 mmol) in THF (1.4 ml) is cooled in a salt/ice bath and oxone (14.5 mg, 0.024 mmol) in water (0.5 ml) is added. After 15 minutes the reaction mixture is allowed to warm to room temperature and after a further 30 minutes more oxone (14.5 mg is added). The mixture is diluted with ethyl acetate/water and the aqueous layer extracted with ethyl acetate. The combined organic layers are washed with brine then dried over magnesium sulfate. Filtration followed by evaporation yields a foam consisting of title compound and 4-[8-(3-Methanesulfonyl-phenyl)-[1,7]naphthyridin-6-yl]-cyclohexanecarboxylic acid. MS (AP+) 395.87

EXAMPLES 9, 13, 17, 18 and 22

Compounds of these Examples are made by an analogous procedure to Example 10 and may be isolated as either the free acid or as a salt, for example the potassium salt.

EXAMPLES 19, 20 and 21

Compounds of these Examples are made by an analogous procedure to Example 11 and may be isolated as either the free acid or as a salt, for example the potassium salt.

The invention claimed is:
1. A compound of formula I

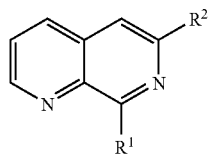

in free or salt form, where
R$^1$ is a monovalent aromatic group having up to 10 carbon atoms, and
R$^2$ is C$_3$-C$_8$-cycloalkyl optionally substituted by at least one substituent selected from C$_1$-C$_4$-alkyl, carboxy, C$_1$-C$_8$-alkoxycarbonyl or aminocarbonyl.

2. A compound according to claim 1, in which
R$^1$ is phenyl substituted by one or two substituents selected from cyano, halogen, carboxy or aminocarbonyl, and optionally by C$_1$-C$_8$-alkoxy, or R$^1$ is phenyl substituted by C$_1$-C$_4$-alkoxy, hydroxy or C$_1$-C$_4$-alkylthio.

3. A compound according to claim 1, in which
R$^1$ is phenyl substituted by one or two substituents selected from cyano, halogen, carboxy or aminocarbonyl meta to the indicated naphthyridine ring and optionally by C$_1$-C$_4$-alkoxy ortho to the indicated naphthyridine ring, or R$^1$ is phenyl substituted by C$_1$-C$_4$-alkoxy meta to the indicated naphthyridine ring, and
R$^2$ is C$_5$-C$_7$-cycloalkyl optionally substituted by at least one substituent selected from carboxy and C$_1$-C$_4$-alkoxycarbonyl.

4. A compound according to claim 1 in which
R$^1$ is phenyl optionally substituted by one, two or three substituents selected from the group consisting of halo, cyano, C$_1$-C$_8$-alkyl, C$_1$-C$_8$-alkylthio, —SO—C$_1$-C$_8$-alkyl, C$_1$-C$_8$-alkoxy and C$_1$-C$_8$-haloalkoxy; and
R$^2$ is C$_3$-C$_8$-cycloalkyl optionally substituted by at least one substituent selected from the group consisting of carboxy and carboxy-C$_1$-C$_8$-alkoxy.

5. A compound according to claim 1, in which
R$^1$ is phenyl optionally substituted by one, two or three substituents selected from the group consisting of halo, cyano, C$_1$-C$_4$-alkyl, C$_1$-C$_4$-alkylthio, —SO—C$_1$-C$_4$-alkyl, C$_1$-C$_4$-alkoxy and C$_1$-C$_4$-haloalkoxy; and
R$^2$ is C$_5$-C$_7$-cycloalkyl optionally substituted by at least one substituent selected from the group consisting of carboxy and carboxy-C$_1$-C$_4$-alkoxy.

6. A compound according to claim 1, which is 4-[8-(3-cyano-phenyl) -[1,7]naphthyridin-6-yl]-cyclohexanecarboxylic acid ethyl ester, 4-[8-(3-cyano-phenyl) -[1,7]naphthyridin-6-yl]-cyclohexanecarboxylic acid, 4-[8-(3-cyano-phenyl)-[1,7]naphthyridin -6-yl]-cyclohexane-carboxylic acid potassium salt, 4-[8-(3-carbamoyl-phenyl)-[1,7]naphthyridin-6-yl]-cyclo-hexanecarboxylic acid, 3-[6-(4-carboxy-cyclohexyl)-[1,7]naphthyridin-8-yl]-benzoic acid, 4-[8-(5-fluoro-2-methoxy-phenyl)-[1,7]naphthyridin-6-yl]-cyclohexanecarboxylic acid ethyl ester, 4-[8-(5-fluoro-2-methoxy-phenyl)-[1 ,7]naphthyridin-6-yl]-cyclohexanecarboxylic acid, or 4-[8-(5-fluoro-2-methoxy-phenyl)-[1 ,7]naphthyridin-6-yl]-cyclohexanecarboxylic acid sodium salt.

7. A compound according to claim 1, in which R$^1$ and R$^2$ are as listed in the following table:

-continued

| R¹ | R² |
|---|---|
| 3-fluorophenyl (methyl) | 4-methylcyclohexanecarboxylic acid |
| 3-chlorophenyl (methyl) | 4-methylcyclohexanecarboxylic acid |
| 3-trifluoromethoxyphenyl (methyl) | 4-methylcyclohexanecarboxylic acid |
| 3-methylthiophenyl (methyl) | 4-methylcyclohexanecarboxylic acid |
| 3-methylsulfinylphenyl (methyl) | 4-methylcyclohexanecarboxylic acid |
| 3-methylphenyl (methyl) | 4-methylcyclohexanecarboxylic acid |
| 3-chloro-4-fluorophenyl (methyl) | 4-methylcyclohexanecarboxylic acid |
| 3-methylphenyl (methyl) | 4-methylcyclohexyloxyacetic acid |
| 3-fluorophenyl (methyl) | 4-methylcyclohexyloxyacetic acid |

| R¹ | R² |
|---|---|
| phenyl (methyl) | 4-methylcyclohexanecarboxylic acid. |

8. A process for the preparation of compounds of formula I in free or salt form which comprises
(i) (A) reacting a compound of formula II $$\text{II}$$

optionally in protected form, where R¹ is as defined in claim 1 and L is a leaving atom or group, with a compound of formula III $$X\text{-}R^2 \qquad \text{III}$$

optionally in protected form, where R² is as defined in claim 1 and X is a leaving atom or group which is reactive with L in formula II to form a direct bond between R² and the indicated naphthyridine ring, followed by deprotection if required, or
(B) reacting a compound of formula I, where R² is cycloalkyl substituted by a C₁-C₈-alkoxycarbonyl group, to convert the alkoxycarbonyl group into a carboxy group, and
(ii) recovering the product in free or salt form.

9. A pharmaceutical composition comprising a compound according to claim 1, optionally together with a pharmaceutically acceptable diluent or carrier.

10. A pharmaceutical composition comprising a compound according to claim 6, optionally together with a pharmaceutically acceptable diluent or carrier.

11. A pharmaceutical composition comprising a compound according to claim 7, optionally together with a pharmaceutically acceptable diluent or carrier.

12. A method of treating an obstructive or inflammatory airways disease in a subject in need of such treatment, which comprises administering to said subject an effective amount of a compound of formula I as defined in claim 1 in free form or in the form of a pharmaceutically acceptable salt.

13. A method of treating an obstructive or inflammatory airways disease in a subject in need of such treatment, which comprises administering to said subject an effective amount of a compound of formula I as defined in claim 6 in free form or in the form of a pharmaceutically acceptable salt.

14. A method of treating an obstructive or inflammatory airways disease in a subject in need of such treatment, which comprises administering to said subject an effective amount of a compound of formula I as defined in claim 7 in free form or in the form of a pharmaceutically acceptable salt.

* * * * *